(12) United States Patent
Wieczorek et al.

(10) Patent No.: US 10,448,909 B2
(45) Date of Patent: Oct. 22, 2019

(54) COMBINED X-RAY AND NUCLEAR IMAGING

(71) Applicant: KONINKLIJKE PHILIPS N.V., Eindhoven (NL)

(72) Inventors: Herfried Karl Wieczorek, Aachen (DE); Andreas Goedicke, Aachen (DE); Peter Lex Alving, Mierlo (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/082,986

(22) PCT Filed: Feb. 28, 2017

(86) PCT No.: PCT/EP2017/054540
§ 371 (c)(1),
(2) Date: Sep. 7, 2018

(87) PCT Pub. No.: WO2017/153198
PCT Pub. Date: Sep. 14, 2017

(65) Prior Publication Data
US 2019/0090827 A1    Mar. 28, 2019

(30) Foreign Application Priority Data
Mar. 8, 2016 (EP) .................................... 16159219

(51) Int. Cl.
*A61B 6/00* (2006.01)
*A61B 6/03* (2006.01)
(Continued)

(52) U.S. Cl.
CPC ............ *A61B 6/4258* (2013.01); *A61B 6/037* (2013.01); *A61B 6/4233* (2013.01);
(Continued)

(58) Field of Classification Search
CPC ..... A61B 6/4291; A61B 6/032; A61B 6/4035; A61B 6/4233; A61B 6/502; A61B 6/037; A61B 6/4258; G01T 1/644; G01T 1/2018
See application file for complete search history.

(56) References Cited

U.S. PATENT DOCUMENTS 4,212,707 A * 7/1980 Tosswill ................. G21K 1/025
205/103
5,864,146 A    1/1999 Karellas
(Continued)

FOREIGN PATENT DOCUMENTS

JP    2010238945 A    10/2010

*Primary Examiner* — Baisakhi Roy
(74) *Attorney, Agent, or Firm* — Larry Liberchuk (57) ABSTRACT

The invention relates to a combined imaging detector (110) for the detection of x-ray and gamma quanta. The combined imaging detector (110) is adapted for simultaneous detection of gamma and x-ray quanta. The combined imaging detector (110) includes an x-ray anti-scatter grid (111), a layer of x-ray scintillator elements (112), a first photodetector array (113), a layer of gamma scintillator elements (114), and a second photodetector array (115) that are arranged in a stacked configuration along a radiation-receiving direction (116). The x-ray anti-scatter grid (111) comprises a plurality of septa ($117_{A, B, C}$) that define a plurality of apertures (118) which are configured to collimate both x-ray quanta and gamma quanta received from the radiation receiving direction (116) such that received gamma quanta are collimated only by the x-ray anti-scatter grid (111). The use of the x-ray anti-scatter grid as a collimator for received gamma quanta results in a significantly lighter combined imaging detector.

12 Claims, 2 Drawing Sheets

(51) Int. Cl.
*G01T 1/161* (2006.01)
*G01T 1/16* (2006.01)
*G21K 1/02* (2006.01)
*G06T 11/00* (2006.01)

(52) U.S. Cl.
CPC .......... *A61B 6/4291* (2013.01); *A61B 6/4417* (2013.01); *A61B 6/4441* (2013.01); *A61B 6/5205* (2013.01); *G01T 1/1603* (2013.01); *G01T 1/1615* (2013.01); *G06T 11/003* (2013.01); *G21K 1/025* (2013.01)

(56) References Cited

U.S. PATENT DOCUMENTS

| | | | |
|---|---|---|---|
| 6,252,938 B1 * | 6/2001 | Tang | G21K 1/025 378/154 |
| 6,448,559 B1 | 9/2002 | Saoudi | |
| 7,218,701 B2 | 5/2007 | Ueno | |
| 8,519,343 B1 * | 8/2013 | Mihailescu | G01T 1/1647 250/367 |
| 2002/0070365 A1 * | 6/2002 | Karellas | A61B 6/06 250/581 |
| 2003/0128801 A1 * | 7/2003 | Eisenberg | A61B 6/032 378/19 |
| 2008/0166063 A1 * | 7/2008 | Zeng | G06T 5/003 382/260 |
| 2009/0257621 A1 * | 10/2009 | Silver | G06K 9/6202 382/103 |
| 2010/0215142 A1 * | 8/2010 | Dafni | A61B 6/032 378/19 |
| 2010/0270462 A1 * | 10/2010 | Nelson | G01T 1/2018 250/252.1 |
| 2013/0237818 A1 | 9/2013 | Herrmann | |
| 2014/0242600 A1 * | 8/2014 | Xing | G01N 21/6458 435/6.18 |
| 2014/0341453 A1 | 11/2014 | Hsu | |
| 2016/0022230 A1 * | 1/2016 | Farbizio | A61B 6/025 378/22 |

* cited by examiner

COMBINED X-RAY AND NUCLEAR IMAGING

FIELD OF THE INVENTION

The invention relates to the detection of x-ray and gamma quanta. It finds application in the medical field, more particularly in the fields of medical imaging and medical interventions, and may be used for example to provide an x-ray image and a corresponding nuclear image of a region of interest.

BACKGROUND OF THE INVENTION

In various medical imaging procedures it is beneficial to provide both an x-ray image and a nuclear image of a region of interest. The x-ray image typically provides structural information indicative of the anatomy of the region of interest. The nuclear image, defined herein to mean an image indicative of radiotracer distribution in an object, is generated based on detected gamma quanta. The nuclear image may for example be a gamma scintigraphy or a SPECT image and typically provides functional, or physiological information relating to the region of interest. Together the two different image types can be used to improve the identification of an underlying pathology during a medical investigation.

Various medical procedures also benefit from a combination of x-ray and nuclear imaging. Selective internal radiation therapy, or SIRT, is one such medical procedure in which radiation is used to treat cancer. SIRT is often used for non-resectable cancers, i.e. cancers that cannot be treated surgically, and involves injecting microspheres of radioactive material into the arteries that supply the tumor. Liver tumours or metastases are often treated in this way. However, in delivering such therapy, a number of workflow steps are required in order to prevent potential side effects. These steps may include the closure of atypical lung and gastrointestinal shunts before injection of Yttrium-90-containing microspheres. This prevents radiation ulcers which might otherwise be triggered by extra-hepatic localization of administered micro-spheres. For this purpose, catheter-based vessel coiling is performed under x-ray guidance during a minimally-invasive procedure. Afterwards, the remaining shunt level towards lungs and gastrointestinal area may be controlled by injection of Technetium $^{99m}$Tc albumin aggregated, i.e. Tc-labeled MAA, into both main liver arteries followed by planar gamma imaging. During this procedure the patient is typically repeatedly transported between a cath lab and SPECT imaging room.

A need therefore exists for imaging systems that are capable of providing both a nuclear image and an x-ray image.

Document US2013/237818A1 discloses a radiation detector having a first detector layer and a second detector layer. Detectors of the first layer include scintillators and light detectors. The detectors of the second detector layer include scintillators and optical detectors. The scintillators of the first layer have a smaller cross-section than the scintillators of the second layers. A group of the first layer scintillators overlay each second group scintillator. In a CT mode, detectors of the first layer detect transmission radiation to generate a CT image with a relatively high resolution and the detectors of the second layer detect PET or SPECT radiation to generate nuclear data for reconstruction into a lower resolution emission image.

Document U.S. Pat. No. 6,448,559 B1 discloses a detector assembly for multi-modality PET/SPEC/CT scanners. The detector assembly comprises a first layer for detecting low energy gamma radiation and x-rays and a second layer for detecting high energy gamma radiation. The first layer is generally transparent to high energy gamma radiation. The detector assembly includes a photodetector in the form of an avalanche photodiode to transform the light signals from the scintillators into electric signals. The detector assembly may be incorporated in a multi-modality PET/SPECT/CT scanner for simultaneous transmission and emission imaging with the same detection geometry. In one example configuration a collimator is positioned in front of the detector assembly to define preferential incidence directions for SPECT photons.

However, in the field of medical imaging, and in the field of medical procedures, there remains a need for improved imaging systems that are capable of providing both a nuclear image and an x-ray image.

SUMMARY OF THE INVENTION

It is an object of the invention to provide a system for providing both a nuclear image and an x-ray image of a region of interest. Thereto a combined imaging detector is provided.

The combined imaging detector is adapted for simultaneous detection of gamma and x-ray quanta. The combined imaging detector includes an x-ray anti-scatter grid, a layer of x-ray scintillator elements for generation of x-ray scintillation light signals in response to detected x-ray quanta, and a first photodetector array configured to receive the x-ray scintillation light signals and to convert said x-ray scintillation light signals into a first group of electrical signals. The combined imaging detector also includes a layer of gamma scintillator elements for generation of gamma scintillation light signals in response to detected gamma quanta, and a second photodetector array configured to receive the gamma scintillation light signals and to convert said gamma scintillation light signals into a second group of electrical signals. Moreover, the x-ray anti-scatter grid, the layer of x-ray scintillator elements, the first photodetector array, the layer of gamma scintillator elements, and the second photodetector array are arranged in a stacked configuration along a radiation-receiving direction. The x-ray anti-scatter grid comprises a plurality of septa that define a plurality of apertures which are configured to collimate both x-ray quanta and gamma quanta received from the radiation receiving direction such that received gamma quanta are collimated only by the x-ray anti-scatter grid.

Conventionally a gamma camera, i.e. a camera that is used to provide a SPECT image or a scintigraphy image, requires a collimator. A gamma camera collimator is a device that is used to limit the angular range of gamma photons that are ultimately detected by the camera. In so doing it ensures that each point in the image corresponds to a unique point in the source. Typically it is attached to the front surface of the gamma camera and is formed from thousands of precisely-aligned holes in a gamma-absorbing material. The holes, i.e. apertures, are thus defined by walls, i.e. septa that are formed from the gamma-absorbing material and operate to limit the angular view of each gamma detector that is positioned behind the collimator. The gamma-absorbing material is typically lead, and the collimator is usually formed by casting or folding lead foil. The lead septa have a depth along the radiation receiving direction, this depth being conventionally determined by the energy of the gamma quanta that the gamma camera is designed to detect. For gamma cameras that detect gamma photons in the range 70-200 keV, septa with a depth of 20-42 mm are typically used and this accounts for some 30-50 kg of the weight of a SPECT collimator.

The inventors have found that in the combined imaging detector described herein in which a gamma detector is stacked behind an x-ray detector with respect to a radiation receiving direction, adequate collimation of gamma photons is provided by an x-ray anti-scatter grid. An x-ray anti-scatter grid, as its name suggests, includes a grid arrangement of septa that define apertures that limit the number of scattered x-ray quanta that are detected by an x-ray detector. Both 1D and 2D anti-scatter grids may be used for this purpose, the former comprising a 1D array of walls, or septa; the latter comprising a 2D array of such septa. As with a collimator, an x-ray anti-scatter grid limits a detector's field of view to x-ray quanta having paths that are substantially parallel to the septa. By decreasing the septa pitch, a 1D anti-scatter grid can be used to limit the x-ray detector field of view to a plane, and a 2D anti-scatter grid can be used to limit the field of view to a line. A 1D anti-scatter grid is conventionally considered to provide adequate anti-scatter performance in x-ray imaging. As in a gamma camera collimator, an x-ray anti-scatter grid is also typically formed from lead, but in contrast its septa typically have a depth in the radiation receiving direction of some 1-5 mm; a depth used in conjunction with 70 keV x-rays. Thus, in the combined imaging detector, received gamma quanta are collimated only by the x-ray anti-scatter grid. Since a gamma camera collimator is omitted, the combined imaging detector is much lighter than, for example, the combined weight of an x-ray detector and a SPECT detector. Consequently the mounting and positioning of the combined detector is greatly simplified. Thus, in one example implementation, the combined detector becomes sufficiently lightweight to be attached to a conventional c-arm.

According to one aspect the combined imaging detector includes a reconstruction unit. The reconstruction unit is configured to generate a reconstructed nuclear image based on the second group of electrical signals. In one configuration the reconstruction unit is configured to generate the reconstructed nuclear image based on a point spread function, PSF, model that represents the gamma scintillation light signal distribution for each aperture of the x-ray anti-scatter grid. Advantageously, by taking account of the PSF during the nuclear image reconstruction process, the resulting image quality, specifically the spatial resolution can be improved. In another configuration the reconstruction unit is configured to generate a reconstructed nuclear scintigraphy image from a measured nuclear scintigraphy image. The reconstruction unit is further configured to generate the reconstructed nuclear scintigraphy image by subtracting a background pixel value, i.e. a reference pixel value, from pixel values in the measured nuclear scintigraphy image. Advantageously by taking account of the background pixel value in this way, image quality can be improved.

Other aspects of the invention are described by the dependent claims.

DETAILED DESCRIPTION OF THE INVENTION

As described above, the present invention provides a system for providing both a nuclear image and an x-ray image of a region of interest. Thereto a combined imaging detector is provided.

Figure 1:
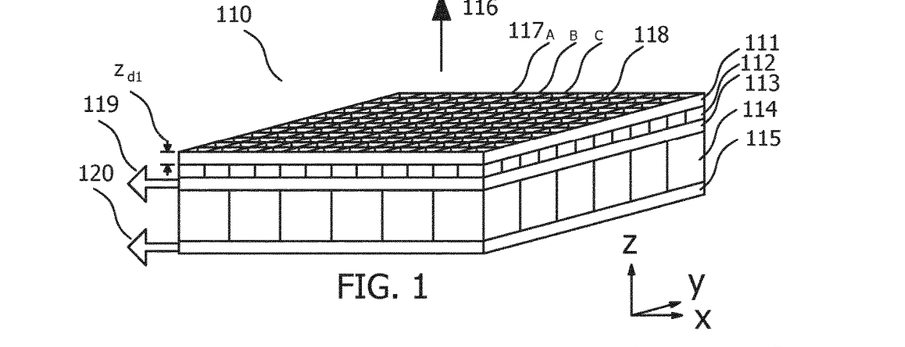
FIG. 1 illustrates a first embodiment of a combined imaging detector 110 that is adapted for simultaneous detection of gamma and x-ray quanta.

FIG. 1 illustrates a first embodiment of a combined imaging detector 110 that is adapted for simultaneous detection of gamma and x-ray quanta. The combined imaging detector includes an x-ray anti-scatter grid 111, a layer of x-ray scintillator elements 112 for generation of x-ray scintillation light signals in response to detected x-ray quanta, and a first photodetector array 113 configured to receive the x-ray scintillation light signals and to convert said x-ray scintillation light signals into a first group of electrical signals. The first group of electrical signals may be output by means of x-ray data bus 119. The combined imaging detector further includes a layer of gamma scintillator elements 114 for generation of gamma scintillation light signals in response to detected gamma quanta, and a second photodetector array 115 configured to receive the gamma scintillation light signals and to convert said gamma scintillation light signals into a second group of electrical signals. The second group of electrical signals may be output by means of gamma data bus 120. Moreover, the x-ray anti-scatter grid 111, the layer of x-ray scintillator elements 112, the first photodetector array 113, the layer of gamma scintillator elements 114, and the second photodetector array 115 are arranged in a stacked configuration along a radiation-receiving direction 116. Combined detector 110 is thus configured to receive gamma and x-ray radiation from radiation-receiving direction 116. Radiation-receiving direction 116 is perpendicular to a plane comprising any of items 111, 112, 113, 114, 115. The term perpendicular as used throughout this specification is intended to mean within approximately ±10 degrees, or within ±5 degrees of exactly perpendicular. X-ray anti-scatter grid 111 comprises a plurality of septa 117$_{A, B, C}$ that define a plurality of apertures 118 which are configured to collimate both x-ray quanta and gamma quanta received from radiation receiving direction 116 such that received gamma quanta are collimated only by the x-ray anti-scatter grid 111. As described above, the combined detector benefits from a significant weight reduction owing to the use of x-ray anti-scatter grid 111 as an anti-scatter grid for the x-ray quanta and as a collimator for the gamma quanta. Furthermore, the combined detector provides simultaneous detection of x-ray and gamma quanta, and the resulting x-ray and nuclear images are self-registered.

As described above, an x-ray anti-scatter grid differs from a gamma camera collimator primarily in that the septa of an x-ray anti-scatter grid have a much shorter depth than the septa of a gamma camera collimator along radiation receiving direction 116. In the examples given above the depth of the septa along radiation receiving direction 116 for an x-ray anti-scatter grid is typically approximately $1/10^{th}$ of that for a gamma camera collimator. This reduction alone gives rise to a corresponding weight reduction in the combined detector. Thus, with reference to x-ray anti-scatter grid 111 in FIG. 1, preferably each septum $117_{A,B,C}$ in the plurality of septa has a depth $z_{d1}$ along the radiation receiving direction 116 that is less than or equal to 5, or 4, or 3, or 2 millimeters.

Another key difference between an x-ray anti-scatter grid and a gamma camera collimator is that the thickness of each septum in a direction perpendicular to the radiation receiving direction is smaller for an x-ray anti-scatter grid. Typically the septum thickness for an x-ray anti-scatter grid is approximately 40 microns. By contrast a gamma camera collimator has a septum thickness of between 150 microns and 1700 microns for the detection of 140 keV gamma quanta. Thus, with reference to x-ray anti-scatter grid 111 in FIG. 1, preferably each septum $117_{A,B,C}$ in the plurality of septa has a thickness in a direction perpendicular to the radiation receiving direction 116 that is less than or equal to 100 microns, or less than or equal to 75 microns, or less than or equal to 50 microns, or less than or equal to 40 microns. These constraints on the septa thickness may be used as an alternative, or in addition to the above depth constraint to define x-ray anti-scatter grid 111.

Another key difference between an x-ray anti-scatter grid and a gamma camera collimator is that an x-ray anti-scatter grid conventionally includes only a 1D array of septa. Such 'slits' that are provided by the septa adequately reduce scatter. By contrast, a collimator for gamma imaging is typically formed from a 2D array of septa. As is described in more detail below, either a 1D x-ray anti-scatter grid that comprises a first set of septa that extend only along a first direction (x), or a 2D x-ray anti-scatter grid may be used as x-ray anti-scatter grid 111.

Further notable differences between an x-ray anti-scatter grid and a gamma camera collimator include i) that the septum pitch of an x-ray anti-scatter grid is typically smaller than the septum pitch in a gamma camera collimator and ii) that the apertures defined by the septa of an x-ray anti-scatter grid are conventionally in the form of slits whereas the apertures defined by the septa of a gamma collimator are typically circular or hexagonal and thus have rotational symmetry around radiation receiving direction 116 with an order exceeding 2, or are circularly symmetric. Exemplary x-ray anti-scatter grids include the N44 r15 grid; i.e. 44 line pair per cm, or 227 micron pitch, with an interspace ratio of 15, and the N24 r12; i.e. 24 line pair per cm, or 417 micron pitch, with an interspace ration of 12. Thus the pitch of an x-ray anti-scatter grid may be less than or equal to 1 mm; and by contrast the pitch of a gamma camera collimator is conventionally greater than 1 mm.

The use of x-ray anti-scatter grid 111 as a collimator for received gamma quanta essentially provides slightly poorer collimation of received gamma photons as compared to a gamma camera collimator, and thus results in a slight degradation in nuclear image quality. In essence the use of the x-ray anti-scatter grid as a collimator for the gamma camera results in a slightly elevated background signal in the nuclear image due to increased septal penetration from obliquely-incident gamma quanta. However the inventors have found that this slight degradation in nuclear image quality is acceptable for many nuclear imaging applications.

The performance of a gamma camera collimator is conventionally described by a point spread function, i.e. a PSF. A PSF describes a detector's response to gamma quanta originating from a point source at a predetermined source-collimator range. This is typically represented by a graphical plot of the detected gamma scintillation light as a function of distance from an axis passing through the source and the centre of the collimator, i.e. off-axis distance. The detected gamma scintillation light is recorded in a plane that is perpendicular to the axis. In such a plot, nuclear image resolution is determined in-part by the width of the PSF.

Figure 4:
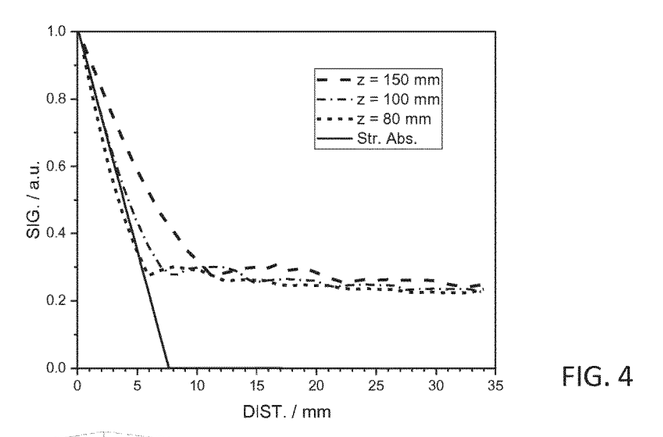
FIG. 4 illustrates three simulated point spread functions in arbitrary units for a 1D x-ray anti-scatter grid for three different source-ASG ranges, z.

Such a plot can be generated for the response of an x-ray anti-scatter grid, i.e. an ASG, to gamma photons. FIG. 4 illustrates three simulated point spread functions in arbitrary units for a 1D x-ray anti-scatter grid for three different source-ASG ranges, z. The simulation parameters were as follows: 44 line pair per cm anti-scatter grid with an interspace ratio of 15 (code: N44 r15); lead ASG strip depth along the radiation receiving direction 2.87 mm; lead ASG strip width perpendicular to the radiation receiving direction 36 µm; i.e. a typical thickness for low line pair grids; septa pitch 216 microns, modified from the typical value of 227 microns to simplify simulation. An additional plot labelled "Str. Abs." in FIG. 4 represents the simulated point spread function for infinite septal absorption for a source-ASG range z=100 mm.

As illustrated in FIG. 4; the three PSF curves reveal a background signal in the order of 20-30% outside the Gaussian-shaped signal. The low-frequency ripples seen on all curves are due to single, twice, triple, etc. penetration of septa. The simulated spatial resolution for this x-ray anti-scatter grid when used as a SPECT collimator for 140 keV radiation (Tc-99m) is 7.34 mm, 9.06 mm, 13.38 mm FWHM for a corresponding source-ASG distance of 80 mm, 100 mm, 150 mm. Maximum penetration of the thin septa was 51%. As noted above, this performance which is achieved with only a 1D x-ray anti-scatter grid, is considered adequate for many nuclear imaging applications. Thus, whilst FIG. 1 illustrates x-ray anti-scatter grid 111 as a 2D array of septa, x-ray anti scatter grid 111 may alternatively be provided by a 1D x-ray anti-scatter grid (211) that comprises a first set of septa that extend only along a first direction (x).

Figure 2:
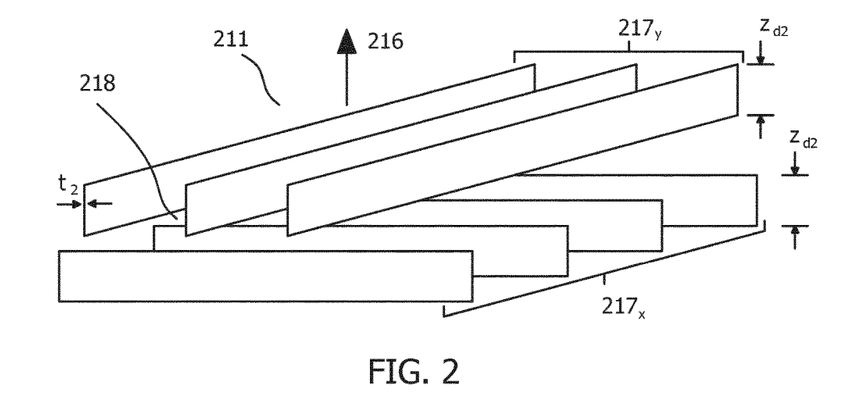
FIG. 2 illustrates a portion of a 2D x-ray anti-scatter grid 211 that is formed from two crossed 1D anti-scatter grids 217$_x$ and 217$_y$.
Figure 5A:
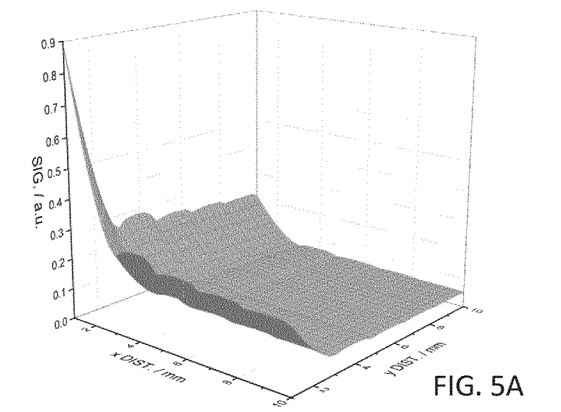
FIG. 5 illustrates simulated point spread functions in arbitrary units for a 2D x-ray anti-scatter grid formed from two crossed 1D anti-scatter grids (A) for a source-ASG range, z=100 mm (B) for a source-ASG range, z=150 mm.
Figure 5B:
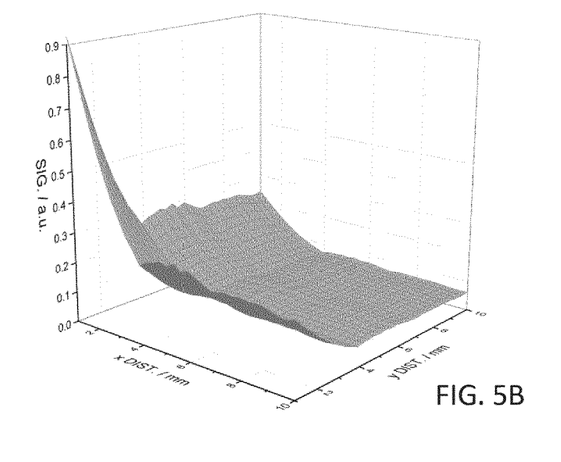

The simulated point spread functions illustrated in FIG. 4 were for a 1D x-ray anti-scatter grid. Similar PSFs are also plotted for a 2D x-ray anti-scatter grid formed from two crossed 1D anti-scatter grids such as anti-scatter grid 211 illustrated in FIG. 2, in FIG. 5. FIG. 2 illustrates a portion of a 2D x-ray anti-scatter grid 211 that is formed from two crossed 1D anti-scatter grids $217_x$ and $217_y$. In FIG. 2, a first set of septa $217_x$ extend along a first direction, x, and a second set of septa $217_y$ extend along a second direction, y. Moreover the first set of septa $217_x$ and the second set of septa $217_y$ are arranged in a stacked configuration along radiation receiving direction 216 such that the first direction, x, and the second direction, y, are mutually transverse. Each septum in FIG. 2 has a depth $z_{d2}$ along radiation receiving direction 216. FIG. 5 illustrates simulated point spread functions in arbitrary units for a 2D x-ray anti-scatter grid formed from two crossed 1D anti-scatter grids (A) for a source-ASG range, z=100 mm (B) for a source-ASG range, z=150 mm. One quadrant of the complete PSF for the gamma scintillation light distribution in a plane perpendicular to the radiation receiving direction is illustrated in FIG. 5. The x and y axes of FIG. 5 represent in millimeters the off-axis distance in orthogonal planes x and y, in the range 0 to 10 mm. The off-axis distance, x, in FIG. 5 labelled "x-DIST./mm" thus corresponds to the off-axis distance in FIG. 4 labelled "DIST./mm". Except for the use of crossed ASG, the simulation parameters were the same as those in FIG. 4. As compared to FIG. 4, in FIG. 5 it can be seen that the magnitude of the background signal is reduced from the 20-30% in FIG. 4 to 5.5% and 6.2% in FIG. 5A and FIG. 5B respectively due to use of the crossed ASG. Thus, the crossed ASG offers improved spatial resolution.

FIG. 5A and FIG. 5B, each representing one quadrant of the whole planar PSF, indicate that without any additional processing, the projection images from point sources results in both a near-constant background signal overlaid with the typical 4-star pattern for rays parallel to the grid axes. The additional low-frequency ripple pattern in the PSF will largely average-out for typical SPECT image resolution during a subsequent nuclear image reconstruction process.

Thus, as with the simulated 1D x-ray anti-scatter grid simulated in FIG. 4, FIG. 5 illustrates that adequate performance for many nuclear imaging applications can also be obtained from a gamma camera in which received gamma quanta are collimated only by a 2D x-ray anti-scatter grid that is formed from two crossed 1D anti-scatter grids. With reference to anti-scatter grid 211 in FIG. 2, preferably each septum $217_x$, $217_y$ in the plurality of septa has a depth $z_{d2}$ along radiation receiving direction 216 that is less than or equal to 5, or 4, or 3, or 2 millimeters. Alternatively, or additionally, each septum $217_{x,\,y}$ in the plurality of septa may have a thickness in a direction perpendicular to the radiation receiving direction 216 that is less than or equal to 100 microns, or less than or equal to 75 microns, or less than or equal to 50 microns, or less than or equal to 40 microns. Moreover, the septa of the two crossed 1D x-ray anti-scatter grids in FIG. 2 can be combined in a single layer to provide a 2D array of septa in a single layer. The performance of such a single layer is expected to be much better than the performance of the 1D and the 2D x-ray anti-scatter grids in FIG. 4 and FIG. 5 in terms of penetration through the septa.

Returning to FIG. 1; additional processing of the second electrical signals from the combined imaging detector, specifically those output at gamma data bus 120, may also be used based on the principles outlined above to further improve the quality of a subsequently-reconstructed nuclear image. Such processing is conventionally performed during image reconstruction by an image reconstruction unit.

Figure 3:
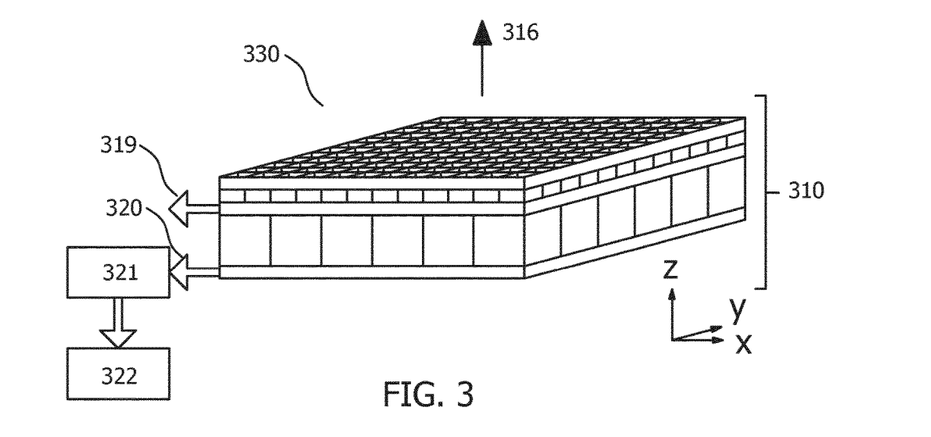
FIG. 3 illustrates a combined imaging detector 310 in combination with a reconstruction unit 321 that is configured to generate a reconstructed nuclear image.

FIG. 3 illustrates a combined imaging detector 310 in combination with a reconstruction unit 321 that is configured to generate a reconstructed nuclear image. Combined imaging detector 310 corresponds to item 110 in FIG. 1 and is likewise configured to receive gamma and x-ray radiation from radiation-receiving direction 316. The nuclear image is generated based on the second group of electrical signals that are received from the second photodetector array by means of gamma bus 320. The image may subsequently be displayed by means of display device 322 that is optionally in communication with reconstruction unit 321.

The form in which the PSF is accounted-for the image reconstruction process may depend to some extent on the type of nuclear image that is acquired. The image may for example be a scintigraphy image; i.e. an image acquired from a gamma detector in a fixed position, or a tomographic, i.e. a SPECT image, indicative of a cross section of an imaged object. In the case of a scintigraphy image, i.e. an image generated during a planar image acquisition mode, the non-zero portion of the PSF, i.e. a background signal, can be subtracted from a measured image. By contrast, in the case of a SPECT image it is preferable to take account of the PSF shape during the image reconstruction process.

Thereto, in one configuration, reconstruction unit 321 is configured to generate a reconstructed nuclear image based on a point spread function model that represents the gamma scintillation light signal distribution for each aperture 118, 218 of x-ray anti-scatter grid 111, 211. The gamma scintillation light signal distribution is modelled for a direction or a plane that is perpendicular to radiation receiving direction 316. By taking account of the PSF during the nuclear image reconstruction process, the resulting image quality, specifically the spatial resolution can be improved. It is noted that, conventionally, when a PSF is used in a nuclear image reconstruction process it is the PSF of a SPECT collimator that is used and not the PSF of an x-ray anti-scatter grid.

Optionally the point spread function model used in the reconstruction process may include, in a direction perpendicular to radiation receiving direction 316, a central lobe portion and a non-zero portion beyond the central lobe. The central lobe portion typically has a peak value in the centre of the aperture. Examples of such a lobe portion, and a non-zero portion, or background portion are illustrated in FIG. 4 between distance=0 and approximately 7 mm, and between distance=approximately 7 and 20 mm. Although FIG. 4 only plots the PSF for the positive x-axis, the central lobe portion is inherent when it is considered that the gamma scintillation light signal distribution in the negative x-axis is a mirrored version of that plotted for the positive x-axis. Similar PSFs can also be plotted for the orthogonal direction to the distance axis in FIG. 4. Moreover, in the reconstruction process, reconstruction unit 321 may be further configured to generate the reconstructed nuclear image by subtracting the non-zero portion from the point spread function. By accounting for the non-zero portion, i.e. the background portion of the PSF in this way, an improved nuclear image can be generated. As shown in FIG. 4 and FIG. 5, typically this non-zero portion can be approximately 5% to 30% of the peak value of the PSF. Conventionally when a PSF is used in an image reconstruction process it is modelled as only a central lobe similar to the straight line in FIG. 4; i.e. there is no non-zero portion in the PSF model beyond the central lobe at all.

Moreover, in SPECT acquisition mode, the PSF may be applied in each loop of an iterative reconstruction process. Each time the loop is executed the noise in the resulting image is reduced. The PSF is preferably applied on the forward projected estimate of the spatial distribution of the radiotracer onto the detector.

Figure 6:
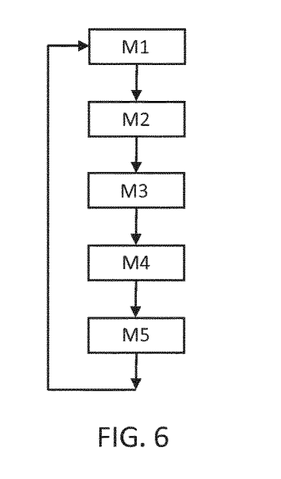
FIG. 6 illustrates various method steps that may be used in combination with the combined imaging detector during an iterative reconstruction process to generate a SPECT image.

FIG. 6 illustrates various method steps that may be used in combination with the combined imaging detector during an iterative reconstruction process to generate a SPECT image. Thus, with reference to FIG. 6, when the reconstructed nuclear image is a SPECT image corresponding to an actual radiotracer distribution in a volume of interest, the reconstruction unit may be configured to generate a reconstructed nuclear image using an iterative reconstruction algorithm that includes the steps of:

providing (M1) an estimate of the radiotracer distribution in the volume of interest;

projecting (M2) the estimated radiotracer distribution onto the combined imaging detector to provide a projected estimated scintillation light distribution;

receiving (M3), based on the second group of electrical signals, signals indicative of a measured scintillation light distribution corresponding to the actual radiotracer distribution;

comparing (M4) the measured scintillation light distribution with the projected estimated scintillation light distribution; and updating (M5) the estimate of the radiotracer distribution in the volume of interest based on the comparing step;

wherein the point spread function model is applied during the step of projecting (M2) the estimated radiotracer distribution.

With reference to FIG. 1, the estimated radiotracer distribution is typically projected onto a plane that includes second photodetector array 115.

Thus, whilst the performance of the x-ray ASG provides adequate collimation of the gamma quanta for some nuclear imaging applications in the absence of the above PSF model, further improved performance, for example that suited to diagnostic SPECT imaging, can be obtained by further taking account of the performance of the ASG through the PSF model.

Furthermore, a computer program product comprising instructions for controlling the combined imaging detector described above, is disclosed. The instructions, when executed on a processor cause the processor to generate a reconstructed SPECT nuclear image corresponding to an actual radiotracer distribution in a volume of interest using an iterative reconstruction algorithm based on the second group of electrical signals and based on a point spread function model that represents the gamma scintillation light signals for each septum in the plurality of septa, comprise the steps of:

providing (M1) an estimate of the radiotracer distribution in the volume of interest;

projecting (M2) the estimated radiotracer distribution onto the combined imaging detector to provide a projected estimated scintillation light distribution;

receiving (M3), based on the second group of electrical signals, signals indicative of a measured scintillation light distribution corresponding to the actual radiotracer distribution;

comparing (M4) the measured scintillation light distribution with the projected estimated scintillation light distribution; and updating (M5) the estimate of the radiotracer distribution in the volume of interest based on the comparing step;

wherein the point spread function model is applied during the step of projecting (M2) the estimated radiotracer distribution.

The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk read only memory "CD-ROM", compact disk read/write "CD-R/W", Blu-Ray™ and DVD.

In an alternative configuration, reconstruction unit 321 in FIG. 3 may be configured to generate a reconstructed nuclear scintigraphy image from a measured nuclear scintigraphy image. In this configuration the measured nuclear scintigraphy image comprises a plurality of pixel values that are generated based on the second group of electrical signals. In this configuration reconstruction unit 321 is further configured to generate the reconstructed nuclear scintigraphy image by subtracting a background pixel value, i.e. a reference pixel value, from the pixel values in the measured nuclear scintigraphy image. By subtracting the background pixel value, an improved nuclear image can be obtained. The subtraction may be performed either in the spatial or frequency domain. Preferably the reconstructed nuclear scintigraphy image corresponds to an object having a boundary, and the background pixel value is the value of a pixel in the measured nuclear scintigraphy image at a point beyond the boundary. Alternatively the background pixel value, i.e. the reference pixel value, that is subtracted may be an estimated value corresponding to a modelled or expected value, or the value of a pixel at or near the edge of the field of view of the gamma camera, for example within 20 or 10 or 5 pixels of the edge of the field of view. Again, when the reconstructed nuclear scintigraphy image corresponds to an object having a boundary, the background pixel value that is subtracted is, furthermore, preferably the value of a pixel in the measured nuclear scintigraphy image at a point beyond the boundary; i.e. the subtracted pixel position lies between the boundary and the edge of the field of view. Clearly the non-negativity signal constraint should be preserved. Other techniques such as 2D de-convolution filtering using an averaged, i.e. location—and depth-independent—PSF may also be applied to improve compensation for directional star pattern artefacts outlined above. The image reconstruction process for a nuclear scintigraphy image can therefore be a more straightforward process than that for a SPECT image.

Various example implementations are now enumerated below:

Example 1

Combined imaging detector (110) for simultaneous detection of gamma and x-ray quanta; the combined imaging detector comprising:

an x-ray anti-scatter grid (111);

a layer of x-ray scintillator elements (112) for generation of x-ray scintillation light signals in response to detected x-ray quanta;

a first photodetector array (113) configured to receive the x-ray scintillation light signals and to convert said x-ray scintillation light signals into a first group of electrical signals;

a layer of gamma scintillator elements (114) for generation of gamma scintillation light signals in response to detected gamma quanta;

a second photodetector array (115) configured to receive the gamma scintillation light signals and to convert said gamma scintillation light signals into a second group of electrical signals;

wherein the x-ray anti-scatter grid (111), the layer of x-ray scintillator elements (112), the first photodetector array (113), the layer of gamma scintillator elements (114), and the second photodetector array (115) are arranged in a stacked configuration along a radiation-receiving direction (116);

wherein the x-ray anti-scatter grid (111) comprises a plurality of septa (117A, B, C) that define a plurality of apertures (118) which are configured to collimate both x-ray quanta and gamma quanta received from the radiation receiving direction (116) such that received gamma quanta are collimated only by the x-ray anti-scatter grid (111).

Example 2

The combined imaging detector of Example 1 wherein the x-ray anti-scatter grid (211) comprises a first set of septa (217x) that extend along a first direction (x), and a second set of septa (217y) that extend along a second direction (y);

wherein the first set of septa (217x) and the second set of septa (217y) are arranged in a stacked configuration along the radiation receiving direction (116, 216) such that the first direction (x) and the second direction (y) are mutually transverse.

Example 3

The combined imaging detector of any one of Examples 1-2 wherein i) each septum (117A,B,C, 217x, 217y) in the plurality of septa has a depth (zd1, zd2) along the radiation receiving direction (116, 216) and the depth (zd1, zd2) is less than or equal to 5 millimeters and/or ii) each septum (117A,B,C, 217x, 217y) in the plurality of septa has a thickness (t2) in a direction perpendicular to the radiation receiving direction (116, 216) and the thickness (t2) is less than or equal to 100 microns.

Example 4

The combined imaging detector of any one of Examples 1-3 further comprising a reconstruction unit (321) configured to generate a reconstructed nuclear image based on the second group of electrical signals;

wherein the reconstruction unit (321) is configured to generate the reconstructed nuclear image based on a point spread function model that represents the gamma scintillation light signal distribution for each aperture (118, 218) of the x-ray anti-scatter grid (111, 211).

Example 5

The combined imaging detector of Example 4 wherein the point spread function model includes, in a direction perpendicular to the radiation receiving direction, a central lobe portion and a non-zero portion beyond the central lobe; and wherein the reconstruction unit is further configured to generate the reconstructed nuclear image by subtracting the non-zero portion from the point spread function.

Example 6

The combined imaging detector of Example 4 or Example 5 wherein the reconstructed nuclear image is a SPECT image corresponding to an actual radiotracer distribution in a volume of interest and wherein the reconstruction unit is configured to generate the reconstructed nuclear image using an iterative reconstruction algorithm that includes the steps of:

providing (M1) an estimate of the radiotracer distribution in the volume of interest;

projecting (M2) the estimated radiotracer distribution onto the combined imaging detector to provide a projected estimated scintillation light distribution;

receiving (M3), based on the second group of electrical signals, signals indicative of a measured scintillation light distribution corresponding to the actual radiotracer distribution;

comparing (M4) the measured scintillation light distribution with the projected estimated scintillation light distribution; and updating (M5) the estimate of the radiotracer distribution in the volume of interest based on the comparing step;

wherein the point spread function model is applied during the step of projecting the estimated radiotracer distribution.

Example 7

The combined imaging detector of any one of Examples 1-3 further comprising a reconstruction unit (321) configured to generate a reconstructed nuclear scintigraphy image from a measured nuclear scintigraphy image comprising a plurality of pixel values, the measured nuclear scintigraphy image being generated based on the second group of electrical signals;

wherein the reconstruction unit (321) is further configured to generate the reconstructed nuclear scintigraphy image by subtracting a reference pixel value from the pixel values in the measured nuclear scintigraphy image.

Example 8

The combined imaging detector of Example 7, wherein the reconstructed nuclear scintigraphy image corresponds to an object having a boundary; and wherein the reference pixel value is the value of a pixel in the measured nuclear scintigraphy image at a point beyond the boundary.

Example 9

The combined imaging detector of Example 7 or Example 8 wherein the combined imaging detector has a field of view for detected gamma quanta; and wherein the reference pixel value is the value of a pixel in the measured nuclear scintigraphy image at a point within 10 pixels of a pixel at the edge of the field of view.

Example 10

The combined imaging detector of any one of Examples 7-9 wherein the subtracting is performed in the frequency domain.

Example 11

C-arm comprising the combined imaging detector of any one of Examples 1-10.

Example 12

Computer program product comprising instructions for controlling the combined imaging detector of any one of Examples 1-3; which instructions, when executed on a processor cause the processor to either:

i) generate a reconstructed SPECT nuclear image corresponding to an actual radiotracer distribution in a volume of interest using an iterative reconstruction algorithm based on the second group of electrical signals and based on a point spread function model that represents the gamma scintillation light signals for each septum in the plurality of septa, wherein the instructions comprise the steps of:

providing (M1) an estimate of the radiotracer distribution in the volume of interest;

projecting (M2) the estimated radiotracer distribution onto the combined imaging detector to provide a projected estimated scintillation light distribution; receiving (M3), based on the second group of electrical signals, signals indicative of a measured scintillation light distribution corresponding to the actual radiotracer distribution;

comparing (M4) the measured scintillation light distribution with the projected estimated scintillation light distribution; and updating (M5) the estimate of the radiotracer distribution in the volume of interest based on the comparing step;

wherein the point spread function model is applied during the step of projecting the estimated radiotracer distribution; or to ii) generate a reconstructed nuclear scintigraphy image from a measured nuclear scintigraphy image comprising a plurality of pixel values, the measured nuclear scintigraphy image being generated based on the second group of electrical signals, wherein the instructions comprise the step of:

subtracting a reference pixel value from the pixel values in the measured nuclear scintigraphy image.

In summary, a combined imaging detector has been described. The combined imaging detector 110 is adapted for simultaneous detection of gamma and x-ray quanta. The combined imaging detector 110 includes an x-ray anti-scatter grid 111, a layer of x-ray scintillator elements 112, a first photodetector array 113, a layer of gamma scintillator elements 114, and a second photodetector array 115 that are arranged in a stacked configuration along a radiation-receiving direction 116. The x-ray anti-scatter grid 111 comprises a plurality of septa 117A, B, c that define a plurality of apertures 118 which are configured to collimate both x-ray quanta and gamma quanta received from the radiation receiving direction 116 such that received gamma quanta are collimated only by the x-ray anti-scatter grid 111.

The invention claimed is:

1. An imaging detector for detecting gamma quanta and x-ray quanta, comprising:

an x-ray anti-scatter grid;

a layer of x-ray scintillator elements configured to generate x-ray scintillation light signals in response to the x-ray quanta;

a first photodetector array configured to convert the x-ray scintillation light signals into a first group of electrical signals;

a layer of gamma scintillator elements configured to generate gamma scintillation light signals in response to the gamma quanta;

a second photodetector array configured to convert the gamma scintillation light signals into a second group of electrical signals;

wherein the x-ray anti-scatter grid, the layer of x-ray scintillator elements, the first photodetector array, the layer of gamma scintillator elements, and the second photodetector array are arranged in a predetermined stacked configuration along a radiation receiving direction; wherein the x-ray anti-scatter grid comprises a plurality of septa that define a plurality of apertures which are configured to collimate the x-ray quanta and the gamma quanta received from the radiation receiving direction, such that the gamma quanta are collimated by the x-ray anti-scatter grid only; and a reconstruction unit configured to generate a reconstructed nuclear scintigraphy image from a measured nuclear scintigraphy image, which is based on the second group of electrical signals, by subtracting a reference pixel value from a pixel value in the measured nuclear scintigraphy image.

2. The imaging detector of claim 1, wherein the plurality of septa comprises a first set of septa that extend along a first direction, and a second set of septa that extend along a second direction;

wherein the first set of septa and the second set of septa are arranged in a stacked configuration along the radiation receiving direction, such that the first direction and the second direction are mutually transverse.

3. The imaging detector of claim 1, wherein each septum in the plurality of septa has a depth along the radiation receiving direction that is less than or equal to approximately 5 millimeters, and/or each septum in the plurality of septa has a thickness in a direction perpendicular to the radiation receiving direction that is less than or equal to approximately 100 microns.

4. The imaging detector of claim 1, wherein the reconstruction unit is further configured to generate the reconstructed nuclear image based on a point spread function model that represents a distribution of the gamma scintillation light signals for each aperture of the x-ray anti-scatter grid.

5. The imaging detector of claim 4, wherein the point spread function model includes, in a direction perpendicular to the radiation receiving direction, a central lobe portion and a non-zero portion beyond the central lobe portion; and wherein the reconstructed nuclear image is generated by subtracting the non-zero portion from the point spread function.

6. The imaging detector of claim 4, wherein the reconstructed nuclear image is a SPECT image corresponding to a radiotracer distribution in a volume of interest, and wherein the reconstruction unit is further configured to generate the reconstructed nuclear image using an iterative reconstruction algorithm that includes:

estimating the radiotracer distribution in the volume of interest;

projecting the estimated radiotracer distribution onto the combined imaging detector to provide a projected estimated scintillation light distribution;

receiving, based on the second group of electrical signals, distribution of the measured scintillation light signals corresponding to the radiotracer distribution;

comparing the distribution of the measured scintillation light signals with the projected estimated scintillation light distribution; and updating the estimated radiotracer distribution in the volume of interest based on the comparing;

wherein the point spread function model is applied when projecting the estimated radiotracer distribution.

7. The imaging detector of claim 1, wherein the reconstructed nuclear scintigraphy image corresponds to an object having a boundary; and wherein the reference pixel value is at a point beyond the boundary in the measured nuclear scintigraphy image.

8. The imaging detector of claim 1, further comprising a field of view for detected gamma quanta; wherein the reference pixel value is in the measured nuclear scintigraphy image at a point within approximately 10 pixels of a pixel at the edge of the field of view.

9. The imaging detector of claim 1, wherein the subtracting is performed in the frequency domain.

10. A C-arm comprising the imaging detector of claim 1.

11. A method for detecting gamma quanta and x-ray quanta, comprising:

provinding an x-ray anti-scatter grid;

generating x-ray scintillation light signals by a layer of x-ray scintillator elements in response to the x-ray quanta;

converting the x-ray scintillation light signals by a first photodetector array into a first group of electrical signals;

generating gamma scintillation light signals by a layer of gamma scintillator elements in response to the gamma quanta;

converting the gamma scintillation light signals by a second photodetector array into a second group of electrical signals; wherein the x-ray anti-scatter grid, the layer of x-ray scintillator elements, the first photodetector array, the layer of gamma scintillator elements, and the second photodetector array are arranged in a predetermined stacked configuration along a radiation receiving direction; wherein the x-ray anti-scatter grid comprises a plurality of septa that define a plurality of apertures which are configured to collimate the x-ray quanta and the gamma quanta received from the radiation receiving direction, such that received gamma quanta are collimated by the x-ray anti-scatter grid only; and generating a reconstructed nuclear scintigraphy image from a measured nuclear scintigraphy image, which is generated based on the second group of electrical signals, by subtracting a reference pixel value from a pixel value in the measured nuclear scintigraphy image.

12. A non-transitory computer-readable medium having one or more executable instructions stored thereon, which, when executed by a processor, cause the processor to perform a method for detecting gamma quanta and x-ray quanta, the method comprising:

providing an x-ray anti-scatter grid;

generating x-ray scintillation light signals by a layer of x-ray scintillator elements in response to the x-ray quanta;

converting the x-ray scintillation light signals by a first photodetector array into a first group of electrical signals;

generating gamma scintillation light signals by a layer of gamma scintillator elements in response to the gamma quanta;

converting the gamma scintillation light signals by a second photodetector array into a second group of electrical signals; wherein the x-ray anti-scatter grid, the layer of x-ray scintillator elements, the first photodetector array, the layer of gamma scintillator elements, and the second photodetector array are arranged in a predetermined stacked configuration along a radiation receiving direction; wherein the x-ray anti-scatter grid comprises a plurality of septa that define a plurality of apertures which are configured to collimate the x-ray quanta and the gamma quanta received from the radiation receiving direction, such that received gamma quanta are collimated by the x-ray anti-scatter grid only; and generating a reconstructed nuclear scintigraphy image from a measured nuclear scintigraphy image, which is generated based on the second group of electrical signals, by subtracting a reference pixel value from a pixel value in the measured nuclear scintigraphy image.

* * * * *